United States Patent [19]

Teraji et al.

[11] 4,397,849

[45] Aug. 9, 1983

[54] BENZOTHIAZINE DERIVATIVES

[75] Inventors: Tsutomu Teraji; Teruo Oku, both of Osaka; Youichi Shiokawa, Takatsuki, all of Japan

[73] Assignee: Fujisawa Pharmaceutical Co., Ltd., Osaka, Japan

[21] Appl. No.: 329,862

[22] Filed: Dec. 11, 1981

[30] Foreign Application Priority Data

Dec. 30, 1980 [GB] United Kingdom ............... 8041520

[51] Int. Cl.[3] ................ C07D 279/16; C07D 417/12; A61K 31/54
[52] U.S. Cl. .................................... 424/246; 544/52; 544/2; 544/3; 544/5; 544/7; 544/8
[58] Field of Search .................... 544/52, 2, 3, 5, 8, 544/7; 424/246

[56] References Cited

U.S. PATENT DOCUMENTS

B 348433  2/1976  Krapcho ...................... 260/244 R
2,863,864  12/1958  Kirchner ............................. 544/52

FOREIGN PATENT DOCUMENTS 603132   8/1960  Canada .................................. 544/52
2912445  10/1980  Fed. Rep. of Germany .
1438225   4/1966  France .................................. 544/52
1373537  11/1974  United Kingdom .
2018754  10/1979  United Kingdom .

OTHER PUBLICATIONS

Journal of Heterocyclic Chemistry, vol. 16, (Dec. 1979), pp. 1503-1522; "Benzothiazinone Dioxides and Their Derivatives", Catsoulacos et al.

*Primary Examiner*—John M. Ford
*Attorney, Agent, or Firm*—Oblon, Fisher, Spivak, McClelland & Maier

[57] ABSTRACT

This invention relates to novel benzothiazine derivatives having therapeutic effect on autoimmune diseases, to processes for preparation of such derivatives, and to pharmaceutical compositions containing such derivatives, the derivatives having the formula:

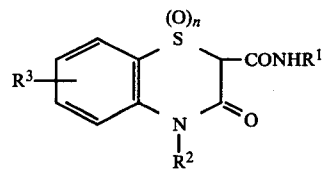

wherein
$R^1$ is lower alkyl which may have one or more substituents selected from carboxy, aryl and carboxy(lower)cycloalkyl; aryl which may have one or more substituents selected from halogen, lower alkyl, halo(lower)alkyl and lower alkoxy; haloarylamino; or heterocyclic group;
$R^2$ is hydrogen, lower alkyl, lower alkylamino(lower)alkyl, aryl or ar(lower)alkyl;
$R^3$ is hydrogen, halogen, lower alkyl or lower alkoxy; and
n is an integer 0 to 2.

6 Claims, No Drawings

BENZOTHIAZINE DERIVATIVES

This invention, as will become apparent from the following description and explanation, relates to new benzothiazine derivatives. More particularly, this invention relates to new benzothiazine derivatives and pharmaceutically acceptable salt thereof, which have therapeutic effect of autoimmune diseases, to processes for preparation thereof, to a pharmaceutical composition comprising the same and to a method of use thereof.

New benzothiazine derivatives of this invention is represented by the following formula (I):

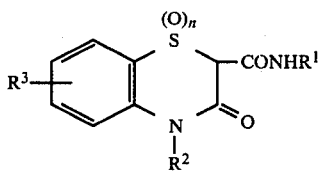

wherein
$R^1$ is lower alkyl which may have one or more substituents selected from carboxy, aryl and carboxy(-lower)cycloalkyl; aryl which may have one or more substituents selected from halogen, lower alkyl, halo(lower)alkyl and lower alkoxy; haloarylamino; or heterocyclic group;

$R^2$ is hydrogen, lower alkyl, lower alkylamino(lower)alkyl, aryl or, ar(lower)alkyl;

$R^3$ is hydrogen, halogen, lower alkyl or lower alkoxy; and n is an integer 0 to 2.

Particulars of the various definitions, which are mentioned hereinabove and hereinafter, and preferred examples thereof are explained in the following.

The term "lower" is intended to mean a group having 1 to 8 carbon atoms, unless otherwise provided.

(1) Re. Lower alkyl which may have one or more substituents selected from carboxy, aryl and carboxy(-lower)cycloalkyl for $R^1$:

Preferred examples of such lower alkyl may include straight and branched one such as methyl, ethyl, propyl, isopropyl, butyl, iso-butyl, t-butyl, pentyl, isopentyl and the like.

Such lower alkyl may have one or more substituents selected from carboxy, aryl and carboxy(lower) cycloalkyl, and preferred examples of lower alkyl having such substituents may include carboxy(lower) alkyl, ar(lower)alkyl and carboxy(lower)cycloalkyl substituted lower alkyl and the like.

Concrete examples of lower alkyl having such substituents are as follows.

Preferred examples of carboxy(lower)alkyl may include 1-carboxy(lower)alkyl such as carboxymethyl, 1-carboxyethyl, 1-carboxypropyl, 1-carboxybutyl, 1-carboxypentyl, 1-carboxyhexyl and the like.

Preferred examples of ar(lower)alkyl may include phenyl(lower)alkyl and more preferably phenyl($C_1$ to $C_5$) alkyl such as benzyl, phenetyl, phenylpropyl and the like.

Preferred examples of carboxy(lower)cycloalkyl substituted(lower)alkyl may include carboxy($C_3$ to $C_7$) cycloalkyl substituted ($C_1$ to $C_5$)alkyl such as carboxycyclopentylmethyl, carboxycyclohexyl methyl, carboxycyclohexylethyl and the like.

(2) Re. Aryl which may have one or more substituents selected from halogen, lower alkyl, halo(lower)alkyl and lower alkoxy for $R^1$:

Preferred examples of such aryl may include phenyl, naphthyl and the like, and such aryl may have one or more substituents selected from halogen, lower alkyl, halo(lower)alkyl and lower alkoxy.

Concrete examples of aryl having such one or more substituent(s) are as follows:

Preferred examples of aryl substituted by halogen (i.e. haloaryl) may include mono or di- halophenyl such as chlorophenyl, dichlorophenyl, bromophenyl, dibromophenyl, fluorophenyl, difluorophenyl and the like.

Preferred examples of aryl substituted by lower alkyl (i.e. lower alkylaryl) may include ($C_1$ to $C_6$) alkylphenyl such as tolyl, xylyl, ethylphenyl, propylphenyl isopropylphenyl, t-butylphenyl, isobutylphenyl and the like.

Preferred examples of aryl substituted by halo(lower)alkyl [i.e. halo(lower)alkylaryl] may include halo($C_1$ to $C_5$)alkylphenyl such as trifluoromethylphenyl and the like.

Preferred examples of aryl substituted by lower alkoxy (i.e. lower alkoxyaryl) may include ($C_1$ to $C_6$) alkoxyphenyl such as methoxyphenyl, 3,4-dimethoxyphenyl, 3,4,5-trimethoxyphenyl, ethoxyphenyl, propoxyphenyl and the like.

Preferred examples of aryl substituted by halogen and halo(lower)alkyl may include halo-halo ($C_1$ to $C_6$)alkylphenyl such as 4-chloro-3-trifluoromethylphenyl and the like.

Preferred examples of aryl substituted by halogen and lower alkoxy may include halo-($C_1$ to $C_6$) alkoxyphenyl such as 4-chloro-3-methoxyphenyl and the like.

(3) Re. Haloarylamino for $R^1$:

Preferred examples of haloarylamino may include halophenylamino such as chlorophenylamino, bromophenylamino, fluorophenylamino and the like.

(4) Re. Heterocyclic group for $R^1$:

Preferred examples of heterocyclic group may include 5 or 6 membered heterocyclic group containing at least one hetero atom selected from nitrogen, oxygen and sulfur, such as pyrrolidinyl, imidazolinyl, thienyl, oxazolyl, thiazolyl, tetrazolyl, pyridyl and the like.

(5) Re. Lower alkyl for $R^2$:

Preferred examples of lower alkyl may include straight and branched ($C_1$ to $C_6$)alkyl such as methyl, ethyl, propyl, isopropyl, butyl, isobutyl, t-butyl, pentyl and the like.

(6) Re. Lower alkylamino(lower)alkyl for $R^2$:

Preferred examples of lower alkylamino(lower) alkyl may include mono or di-($C_1$ to $C_6$)alkylamino($C_1$ to $C_6$)alkyl such as mono- or dimethylaminomethyl, mono- or di-methylaminoethyl, mono-or di-methylaminopropyl, mono- or di-ethylaminomethyl, mono or di-ethylaminoethyl, mono- or di-ethylaminopropyl and the like.

(7) Re. Aryl for $R^2$:

Preferred examples of aryl may include phenyl, tolyl, naphthyl and the like.

(8) Re. Ar(lower)alkyl for $R^2$:

Preferred examples of ar(lower)alkyl may include the same as those illustrated for ar(lower)alkyl for $R^1$.

(9) Re. Halogen for $R^3$:

Preferred examples of halogen may include fluorine, bromine, chlorine,, and iodine.

(10) Re. Lower alkoxy for $R^3$:

Preferred examples of lower alkoxy may include ($C_1$ to $C_5$)alkoxy such as methoxy, ethoxy, propoxy, isopropoxy, butoxy, t-butoxy and the like.

(11) Re. Lower alkyl for $R^3$:

Preferred examples of lower alkyl may include the same as those illustrated for lower alkyl for $R^1$.

A pharmaceutically acceptable salt of the new benzothiazine derivatives of the formula (I) may include a salt with an inorganic or organic base such as an alkali metal salt (e.g. sodium salt, potassium salt, etc.), an alkaline earth metal salt (e.g. calcium salt, etc.), ammonium salt, ethanolamine salt, triethylamine salt, dicyclohexylamine salt and the like, and an acid addition salt with organic or inorganic acid such as methane sulfonate, hydrochloride, sulfate, nitrate, phosphate and the like.

As to the object compound (I) of this invention, it is to be noted that there can often be obtained a keto-enol type tautomerization between the isomers represented by the partial molecular structures (A) and (B).

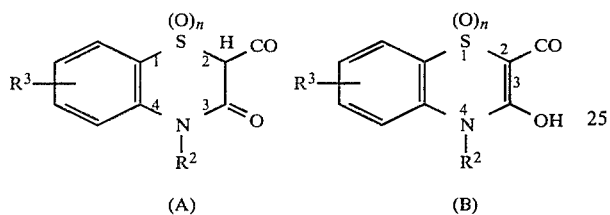

That is, the compound of this invention is generally provided as a enolate compound of the formula (I') in the presence of a base and the enolate compound provides the corresponding keto-form of the formula (I) by treatment with an acid. This observation is described in the working examples of this invention, and can be illustrated by the following scheme:

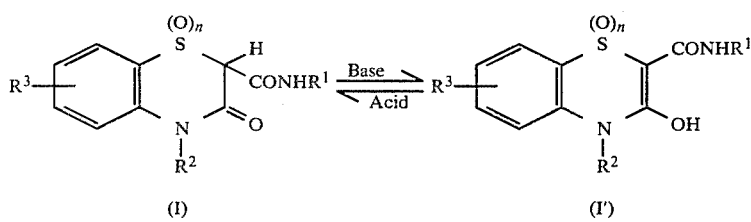

Accordingly, the enolate (I') per se can be understood to be the same compound to (I), and both of the enol and keto forms of the compound concerning of this invention will be inclusively represented by one formula of the keto structure throughout this specification and claim(s), only for convenience sake. And accordingly, it is to be noted that the enolate (I') should also be included within the scope of this invention.

The compound (I) of this invention can be prepared by various methods, details of which will be apparent from the following descriptions.

(1) Process 1:

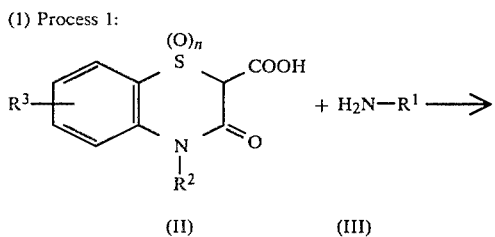

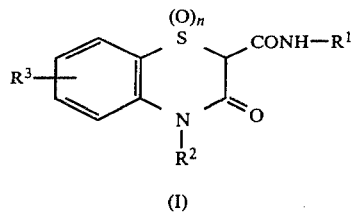

(2) Process 2:

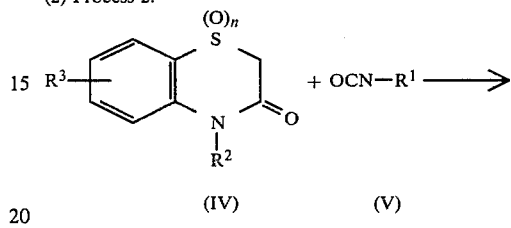

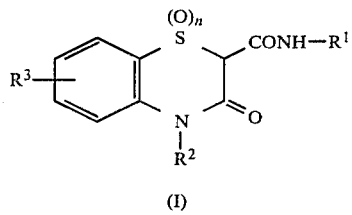

(3) Process 3:

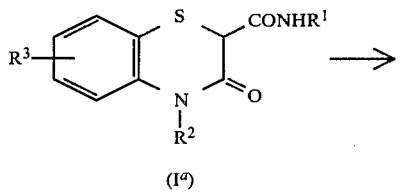

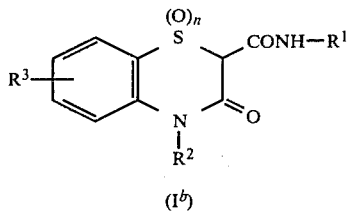

In the above formulae, m' is an integer 1 or 2, and $R^1$, $R^2$, $R^3$ and n are each as defined above.

The processes 1 to 3 for preparation of the new benzothiazine derivatives (I) of this invention are explained in detail in the following.

(1) Process 1:

The compound (I) or a salt thereof can be prepared by reacting the compound (II) or its derivative at the carboxy or a salt thereof with compound (III) or a salt thereof.

Suitable salt of the starting compounds (II) and (III) may include the same one as illustrated for the compound (I).

Suitable derivative of the compound (II) may include, for example, an acid halide, an acid anhydride, a mixed anhydride, an ester, and the like, and preferably an ester with a hydroxy compound such as alkanol (e.g. methanol, ethanol, propanol, etc.) and the like.

The suitable derivative can optionally be selected from the above according to the kinds of the compounds (II) to be used practically.

This reaction may be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium t-butoxide, etc.), alkali metal alkanoic acid (e.g. sodium acetate, etc.), trialkylamine (e.g. triethylamine, etc.), pyridine compound (e.g. pyridine, lutidine, picoline, etc.), quinoline, 1,8-diazabicyclo[5,4,0]undec-7-ene, and the like.

In case that the compound (II) is used in a form of the free acid or a salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1 N-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence to the reaction such as acetone, dioxane, acetonitrile, chloroform, benzene, methylene chloride, ethylene chloride, tetrahydrofuran, ethyl acetate, N,N-dimethylformamide, pyridine, hexamethylphosphoramide, xylene, toluene, etc., or a mixture thereof.

Among these solvents, hydrophilic solvents may be used in a mixture with water.

The reaction temperature is not critical and the reaction is usually carried out at room temperature to under heating.

(2) Process 2

The compound (I) can also be prepared by reacting the compound (IV) with isocyanate compound (V).

The reaction is usually carried out in a conventional solvent such as N,N-dimethylformamide, N,N-dimethylacetamide, tetrahydrofuran, acetonitrile, or any other solvent which does not adversely influence to the reaction.

The reaction is preferably carried out in the presence of an organic or inorganic base and suitable examples of such base include the same one as illustrated for Process 1.

The reaction temperature is not critical and the reaction is preferably carried out under cooling to warming.

(3) Process 3

A compound ($I^a$) or its salt can also be prepared by oxidizing a compound ($I^b$) or its salt with an oxidizing agent.

The reaction is usually carried out in a conventional solvent such as N,N-dimethylformamide, chloroform or any other solvent which does not adversely influence to the reaction.

Preferred examples of the oxidizing agent may include potassium permanganate, organic peracid such as metachloroperbenzoic acid, hydrogen peroxide or the like.

The reaction temperature is not critical and the reaction is preferably carried out under cooling to warming.

Starting compound (II) can be prepared by, for example, the following method.

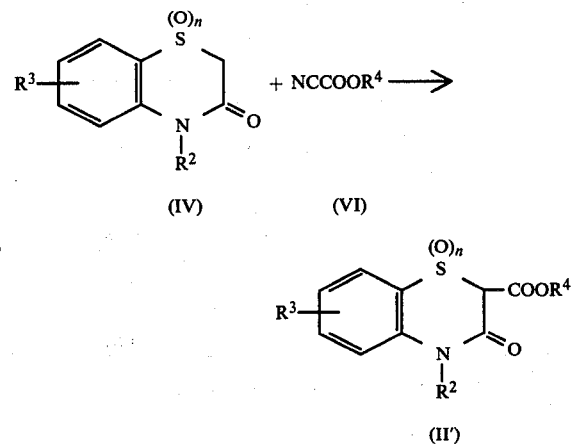

wherein $R^4$ is an ester forming group, and $R^2$, $R^3$ and n are each as defined above.

Preferred examples of an ester forming group may include a conventional one such as alkyl (e.g. methyl, ethyl, propyl, isopropyl, butyl, t-butyl, etc.), aryl (e.g. phenyl, tolyl, xylyl, etc.), aralkyl (e.g. benzyl, diphenylmethyl, phenethyl, etc.).

The compound (II') can be prepared by reacting the compound (IV) with the compound (VI).

The reaction is usually carried out in a conventional solvent such as dimethylformamide, dimethylacetamide, tetrahydrofuran or any other solvent which does not adversely influence to the reaction.

The reaction temperature is not critical and the reaction is usually carried out under cooling to warming.

The ester forming group for $R^4$ of the compound (II') thus prepared may be removed to give a compound (II).

Removal of such an ester forming group may be carried out in a conventional manner such as hydrolysis, reduction or the like.

The new benzothiazin derivatives (I) and its pharmaceutically acceptable salts of this invention have been found to possess inhibitory effect of contact hypersensitivity and accordingly are useful for the therapeutic treatment of steroid-effective diseases, for example, autoimmune diseases.

For the purpose of showing pharmaceutical utility of the new benzothiazine derivatives (I), pharmacological test data thereof is illustrated in the following.

Contact hypersensitivity in the mouse.
Method:

Ten male ICR-JCL mice were used per group. Mice were sensitized by application of 7% picryl chloride-alcohol solution on the shaved abdominal skin two times at an interval of 7 days.

7 Days after the last application of picryl chloride, 1% picryl chloride-olive oil solution was applied on the ear.

The thickness of the ear was measured with a dial thickness gauge before and 24 hr., 48 hr. after challenge. A degree of swelling of the ear was a measure of the hypersensitivity.

The drugs(dose: 100 mg/kg) were given orally 1 hour before and 24 hours after ear painting.
Result:
The test results are shown in the following table.

| Test Compound (Example No.) | Inhibitory percent of increase of ear thickness (%) | |
| --- | --- | --- |
| | 24 hr. | 48 hr. |
| 1 | 56.2** | 61.9** |
| 6 | 37.3* | — |
| 10 | — | 28.6* |
| 11 | — | 35.4* |
| 14 | 41.2** | 49.2** |
| 21 | 56.7** | 38.9** |
| 22 | 48.4* | 47.9** |
| 23 | 42.4** | 55.8** |
| 26 | — | 39.5* |
| 30 | 58.7** | 50.0* |
| 31 | 56.2** | 38.9* |
| 32 | — | 39.2* |
| 36 | 30.7 | 32.8* |
| 37 | — | 32.8* |
| 44 | 41.3* | 46.6* |
| 45 | — | 41.4** |

Note:
*Significance was calculated by Student's t-test; $P < 0.05$
**Significance was calculated by Student's t-test; $P < 0.01$ The pharmaceutical composition of this invention can be used in the form of a pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferable to apply it by intravenous, intramuscular or oral administration. While the dosage or therapeutically effective amount of the object compound of this invention varies from and also depends upon the age and condition of each individual patient to be treated, a daily dose of about 1–1000 mg of the active ingredient/kg of a human being or an animal is generally give for treating diseases, and an average single dose of about 50 mg, 100 mg, 250 mg, and 500 mg is generally administered.

The following examples are given for purpose of illustrating this invention.

PREPARATION 1

To a suspension of sodium hydride (5.13 g, 60% oil dispersion, washed with dry petroleum ether) in dimethylformamide (110 ml) was added 7-chloro-4-methyl-2H-1,4-benzothiazin-3(4H)one 1,1-dioxide (30 g) at 5° to 10° C. The mixture was allowed to warm to room temperature and stirred for 15 minutes for the preparation of the sodium salt. The reaction mixture was then cooled in an ice bath and a solution of ethyl cyanoformate (16.29 g) in dimethylformamide (15 ml) was added dropwise over 30 minutes. After being stirred for one hour, the mixture was quenched with acetic acid (14 ml), poured into ice water, and extracted with ethyl acetate. The organic layer was washed with water, dried over magnesium sulfate, and evaporated under reduced pressure. The oily residue was crystallized from ethanol to afford 31 g of 7-chloro-2-ethoxycarbonyl-4-methyl-2H-1,4-benzothiazin-3(4H)one 1,1-dioxide, mp 86° to 91° C. (melt).

IR (Nujol): 3100, 1750, 1740, 1665, 1335 cm$^{-1}$

NMR (CDCl$_3$) ppm:1.24 (3H, t, J=7 Hz), 3.54 (3H, s), 4.18 (2H, q, J=7 Hz), 4.99 (1H, s), 7.26 (1H, d, J=8 Hz), 7.64 (1H, dd, J=2 Hz, 9 Hz), 7.84 (1H, d, J=2 Hz).

Preparation 2

2-Ethoxycarbonyl-7-fluoro-4-methyl-2H-1,4-benzothiazin-3(4H)one 1,1-dioxide was prepared substantially in the same manner as Preparation 1.

mp 87° to 89° C. (melt).

IR (Nujol): 1740, 1670 cm$^{-1}$.

NMR (DMSO-d$_6$) ppm: 1.13 (3H, t, J=7 Hz), 3.48 (3H, s), 4.22 (2H, q, J=7 Hz), 6.28 (1H, s), 7.60–7.90 (3H, m).

PREPARATION 3

2-Ethoxycarbonyl-7-methoxy-4-methyl-2H-1,4-benzothiazin-3(4H)one 1,1-dioxide was prepared substantially in the same manner as Preparation 1.

mp 160° to 162° C. (melt).

IR (Nujol): 1750, 1680 cm$^{-1}$.

NMR (CDCl$_3$) ppm: 1.20 (3H, t, J=7.5 Hz), 3.50 (3H, s), 3.86 (3H, s), 4.17 (2H, q, J=7.5 Hz), 4.95 (1H, s), 7.20–7.40 (3H, m).

PREPARATION 4

2-Ethoxycarbonyl-6-chloro-4-methyl-2H-1,4-benzothiazin-3(4H)one 1,1-dioxide was prepared substantially in the same manner as Preparation 1.

mp 134° to 136° C. (melt).

IR (Nujol): 3100, 1740, 1680, 1585 cm$^{-1}$.

NMR (DMSO-d$_6$) ppm: 1.13 (3H, t, J=7 Hz), 3.50 (3H, s), 4.21 (2H, q, J=7 Hz), 6.27 (1H, s), 7.50 (1H, dd, J=2 Hz, 8 Hz), 7.78 (1H, d, J=2 Hz), 7.92 (1H, d, J=8 Hz).

Preparation 5

2-Ethoxycarbonyl-4-methyl-2H-1,4-benzothiazin-3(4H)one 1,1-dioxide was prepared substantially in the same manner as Preparation 1.
mp 95° to 97° C. (melt).
IR (Nujol): 3100, 1740, 1670, 1590 cm$^{-1}$.
NMR (DMSO-d$_6$) ppm: 1.10 (3H, t, J=7 Hz), 3.48 (3H, s), 4.18 (2H, q, J=7Hz), 6.13 (1H, s), 7.30–8.00 (4H, m).

PREPARATION 6

2-Ethoxycarbonyl-4-propyl-2H-1,4-benzothiazin-3(4H)one 1,1-dioxide was prepared substantially in the same manner as Preparation 1.
mp 107° to 110° C. (melt).
IR (Nujol): 1735, 1680 cm$^{-1}$.
NMR (CDCl$_3$) ppm: 0.80–1.31 (6H, m), 1.50–2.00 (2H, m), 3.90–4.40 (4H, m), 4.98 (1H, s), 7.20–8.10 (4H, m).

EXAMPLE 1

To a solution of 1,8-diazabicyclo-[5,4,0]undec-7-ene (14.12 g) in dimethylformamide (111 ml) was added, dropwise in 10 minutes, a solution of 7-chloro-4-methyl-2H-1,4-benzothiazin-3(4H)one 1,1-dioxide (22.8 g) and 4-fluorophenylisocyanate (12.82 g) in dimethylformamide (111.4 ml) at room temperature. After being stirred for one hour, the mixture was poured into 1% hydrochloric acid (1 l). The separated solids were collected by filtration and washed with water. The wet solids were dissolved in ethyl acetate. The mixture was washed with 1% hydrochloric acid, with water, dried over magnesium sulfate, and evaporated under reduced pressure. The residue was crystallized from diethyl ether to yield 24.3 g of 7-chloro-2-(4-fluorophenylcarbamoyl)-4-methyl-2H-1,4-benzothiazin-3(4H)one 1,1-dioxide.

The crystals were purified by recrystallization from ethyl acetate-n-hexane.
mp 205° C. (melt).
IR (Nujol): 3300, 1625 cm$^{-1}$.
NMR (DMSO-d$_6$) ppm: 3.53 (3H, s), 5.63 (1H, s), 7.01–8.03 (7H, m), 10.90 (1H, s).

EXAMPLE 2

2-(3-Chlorophenylcarbamoyl)-4-(3-dimethylamino)-propyl-2H-1,4-benzothiazin-3(4H)one 1,1-dioxide was prepared substantially in the same manner as Example 1.
mp 237° C. (dec.).
IR (Nujol): 1600, 1580 cm$^{-1}$.
NMR (DMSO-d$_6$+DCl) ppm: 2.00–2.50 (2H, m), 2.88 (6H, s), 3.10–3.50 (2H, m), 4.00–4.50 (2H, m), 7.10–8.00 (8H, m).

EXAMPLE 3

2-(4-Chlorophenylcarbamoyl)-4-(3-dimethylamino)-propyl-2H-1,4-benzothiazin-3(4H)one 1,1-dioxide was prepared substantially in the same manner as Example 1.
mp 200° C. (dec.).
NMR (DMSO-d$_6$+DCl) ppm: 1.80–2.60 (2H, m), 2.87 (6H, s), 3.00–3.50 (2H, m), 4.00–4.50 (2H, m), 7.40–8.00 (8H, m).
IR (Nujol): 3600, 3500, 2700, 1600 cm$^{-1}$.

EXAMPLE 4

4-Methyl-2-phenylcarbamoyl-2H-1,4-benzothiazin-3(4H)one 1,1-dioxide was prepared substantially in the same manner as Example 1.
mp 223° to 226° C. (dec.).
IR (Nujol): 3400, 1700, 1685 cm$^{-1}$.
NMR (DMSO-d$_6$) ppm: 3.53 (3H, s), 5.60 (1H, s), 7.10–8.08 (9H, m), 10.83 (1H, b.s).

EXAMPLE 5

A mixture of 7-chloro-2-ethoxycarbonyl-4-methyl-2H-1,4-benzothiazin-3(4H)one 1,1-dioxide (46.9 g), 4-fluoroaniline (37.71 g), and xylene (470 ml) was refluxed under nitrogen for 3 hours. After the mixture was cooled to room temperature, the precipitates were collected by filtration and washed with diethyl ether. The precipitates dissolved in hot methanol (1.6 l) were treated with saturated methanolic hydrogen chloride (250 ml) for 15 minutes. The solvent was evaporated under reduced pressure and the residue was dissolved in ethyl acetate.

The solution was washed with 1% hydrochloric acid, water, dried, and evaporated under reduced pressure. The residue was crystallized from diethyl ether to yield 43.1 g of 7-chloro-2-(4-fluorophenylcarbamoyl)-4-methyl-2H-1,4-benzothiazin-3(4H)one 1,1-dioxide. The crystals were identified with authentic sample of Example 1.

EXAMPLE 6

2-(3,4-Dichlorophenylcarbamoyl)-7-fluoro-4-methyl-2H-1,4-benzothiazin-3(4H)one 1,1-dioxide was prepared substantially in the same manner as Example 5.
mp 180° to 182° C. (melt).
IR (Nujol): 3300, 1690, 1680, 1650 cm$^{-1}$.
NMR (DMSO-d$_6$) ppm: 3.52 (3H, s), 5.62 (1H, s), 7.30–7.90 (6H, m), 11.1 (1H, s).

EXAMPLE 7

7-Fluoro-4-methyl-2-(4-trifluoromethylphenylcarbamoyl)-2H-1,4-benzothiazin-3(4H)one 1,1-dioxide was prepared substantially in the same manner as Example 5.
mp 146° to 148° C. (melt).
IR (Nujol): 3300, 3100, 1620, 1610 cm$^{-1}$.
NMR (DMSO-d$_6$) ppm: 3.52 (3H, s), 5.65 (1H, s), 7.40–8.00 (7H, m), 11.17 (1H, s).

EXAMPLE 8

7-Fluoro-2-(4-fluorophenylcarbamoyl)-4-methyl-2H-1,4-benzothiazin-3(4H)one 1,1-dioxide was prepared substantially in the same manner as Example 5.
mp 153° to 155° C. (melt).
IR (Nujol): 3300, 1680, 1660, 1560 cm$^{-1}$.
NMR (DMSO-d$_6$) ppm: 3.51 (3H, s), 5.57 (1H, m), 7.00–7.90 (7H, m), 10.83 (1H, s).

EXAMPLE 9

2-(5-Carboxypentylcarbamoyl)-7-methoxy-4-methyl-2H-1,4-benzothiazin-3(4H)one 1,1-dioxide was prepared substantially in the same manner as Example 5.
mp 110° to 112° C. (melt).
IR (Nujol): 3300, 3100, 1710, 1670, 1640 cm$^{-1}$.
NMR (DMSO-d$_6$) ppm: 1.0–1.80 (6H, m), 2.0–2.50 (2H, m), 2.80–3.30 (2H, m), 3.43 (3H, s), 3.85 (3H, s), 5.30 (1H, s), 7.30–7.70 (3H, m), 8.50 (1H, brs), 11.90 (1H, brs).

EXAMPLE 10

2-(3,4-Dichlorophenylcarbamoyl)-7-methoxy-4-methyl-2H-1,4-benzothiazin-3(4H)one 1,1-dioxide was prepared substantially in the same manner as Example 5.

mp 230° to 233° C. (melt).

IR (Nujol): 3300, 3200, 3100, 1695, 1660, 1605 cm$^{-1}$.

NMR (DMSO-d$_6$) ppm: 3.50 (3H, s), 3.88 (3H, s), 5.52 (1H, s), 7.30–7.90 (6H, m), 11.15 (1H, s).

EXAMPLE 11

7-Methoxy-4-methyl-2-(3-trifluoromethylphenylcarbamoyl)-2H-1,4-benzothiazin-3(4H)one 1,1-dioxide was prepared substantially in the same manner as Example 5.

mp 165° to 167.5° C. (melt).

IR (Nujol): 3280, 3200, 3100, 1680, 1655 cm$^{-1}$.

NMR (DMSO-d$_6$) ppm: 3.50 (3H, s), 3.87 (3H, s), 5.52 (1H, s), 7.30–7.80 (6H, m), 7.90 (1H, brs), 11.60 (1H, brs).

EXAMPLE 12

2-(4-Fluorophenylcarbamoyl)-7-methoxy-4-methyl-2H-1,4-benzothiazin-3(4H)one 1,1-dioxide was prepared substantially in the same manner as Example 5.

mp 202° to 204° C. (melt).

IR (Nujol): 3280, 3210, 3150, 3100, 1665, 1650 cm$^{-1}$.

NMR (DMSO-d$_6$) ppm: 3.47 (3H, s), 3.85 (3H, s), 5.47 (1H, s), 7.00–7.70 (7H, m), 10.65 (1H, brs).

EXAMPLE 13

7-Chloro-2-(3,4-dichlorophenylcarbamoyl)-4-methyl-2H-1,4-benzothiazin-3(4H)one 1,1-dioxide was prepared substantially in the same manner as Example 5.

mp 176° to 178° C. (melt).

IR (Nujol): 3300, 1610 cm$^{-1}$.

NMR (DMSO-d$_6$) ppm: 3.52 (3H, s), 5.60 (1H, s), 7.30–8.00 (6H, m), 11.19 (1H, s).

EXAMPLE 14

7-Chloro-4-methyl-2-(3-trifluoromethylphenylcarbamoyl)-2H-1,4-benzothiazin-3(4H)one 1,1-dioxide was prepared substantially in the same manner as Example 5.

mp 170° to 172° C. (melt).

IR (Nujol): 3260, 3200, 3100, 3140, 1700, 1660, 1620 cm$^{-1}$.

NMR (DMSO-d$_6$) ppm: 3.53 (3H, s), 5.67 (1H, s), 7.50–8.10 (7H, m), 11.15 (1H, brs).

EXAMPLE 15

6-Chloro-2-(4-chloro-3-trifluoromethylphenylcarbamoyl)-4-methyl-2H-1,4-benzothiazin-3(4H)one 1,1-dioxide was prepared substantially in the same manner as Example 5.

mp 220° to 222° C. (melt).

IR (Nujol): 3300, 3200, 3120, 3100, 1700, 1660, 1610 cm$^{-1}$.

NMR (DMSO-d$_6$) ppm: 3.52 (3H, s), 5.55 (1H, brs), 7.40–8.00 (6H, m), 11.35 (1H, brs).

EXAMPLE 16

2-(5-Carboxypentylcarbamoyl)-6-chloro-4-methyl-2H-1,4-benzothiazin-3(4H)one 1,1-dioxide was prepared substantially in the same manner as Example 5.

mp 137° to 139° C. (melt).

IR (Nujol): 3360, 3100, 1725, 1680, 1650 cm$^{-1}$.

NMR (DMSO-d$_6$) ppm: 1.20–1.80 (6H, m), 2.0–2.50 (2H, m), 2.80–3.40 (2H, m), 3.45 (3H, s), 5.37 (1H, s), 7.40 (1H, dd, J=2 Hz, 8 Hz), 7.67 (1H, d, J=2 Hz), 7.82 (1H, d, J=8 Hz), 8.65 (1H, brs).

EXAMPLE 17

2-(4-Methoxyphenylcarbamoyl)-4-methyl-2H-1,4-benzothiazin-3(4H)one 1,1-dioxide was prepared substantially in the same manner as Example 5.

mp 181° to 183° C. (melt).

IR (Nujol): 3300, 1670, 1640 cm$^{-1}$.

NMR (DMSO-d$_6$) ppm: 3.48 (3H, s), 3.69 (3H, s), 5.48 (1H, s), 6.84 (2H, J=8.5 Hz), 7.36 (2H, d, J=8.5 Hz), 7.40–7.90 (4H, m), 10.56 (1H, s).

EXAMPLE 18

2-(3-Methoxyphenylcarbamoyl)-4-methyl-2H-1,4-benzothiazin-3(4H)one 1,1-dioxide was prepared substantially in the same manner as Example 5.

mp 197° to 199° C. (melt)

IR (Nujol): 3300, 1680, 1660, 1590 cm$^{-1}$.

NMR (DMSO-d$_6$) ppm: 3.50 (3H, s), 3.70 (3H, s), 5.55 (1H, s), 6.60–8.00 (8H, m), 10.55 (1H, s).

EXAMPLE 19

2-(2,4-Difluorophenylcarbamoyl)-4-methyl-2H-1,4-benzothiazin-3(4H)one 1,1-dioxide was prepared substantially in the same manner as Example 5.

mp 192° to 194° C. (melt).

IR (Nujol): 3300, 1700, 1660, 1640 cm$^{-1}$.

NMR (DMSO-d$_6$) ppm: 3.53 (3H, s), 5.87 (1H, s), 6.80–8.00 (7H, m), 10.58 (1H, s).

EXAMPLE 20

4-Methyl-2-(3-trifluoromethylphenylcarbamoyl)-2H-1,4-benzothiazin-3(4H)one 1,1-dioxide was prepared substantially in the same manner as Example 5.

mp 101° to 103° C. (melt).

IR (Nujol): 3310, 1700, 1680 cm$^{-1}$.

NMR (DMSO-d$_6$): 3.55 (3H, s), 5.62 (1H, s), 7.40–8.00 (8H, m), 11.23 (1H, s).

EXAMPLE 21

2-3,4-Dichlorophenylcarbamoyl)-4-methyl-2H-1,4-benzothiazin-3(4H)one 1,1-dioxide was prepared substantially in the same manner as Example 5.

mp 150° C. (dec.).

IR (Nujol): 3300, 1700, 1680, 1600 cm$^{-1}$.

NMR (DMSO-d$_6$) ppm: 3.55 (3H, s), 5.60 (1H, s), 7.30–8.10 (7H, m), 11.17 (1H, s).

EXAMPLE 22

2-(4-Chlorophenylcarbamoyl)-4-methyl-2H-1,4-benzothiazin-3(4H)one 1,1-dioxide was prepared substantially in the same manner as Example 5.

mp 220° to 222° C. (melt).

IR (Nujol): 3300, 1670, 1650 cm$^{-1}$.

NMR (DMSO-d$_6$) ppm: 3.51 (3H, s), 5.57 (1H, s), 7.30–8.10 (8H, m), 11.00 (1H, brs).

EXAMPLE 23

2-(4-Fluorophenylcarbamoyl)-4-methyl-2H-1,4-benzothiazin-3(4H)one 1,1-dioxide was prepared substantially in the same manner as Example 5.

mp 189° to 192° C. (melt).

IR (Nujol): 3300, 1670, 1650 cm$^{-1}$.

NMR (DMSO-d$_6$) ppm: 3.50 (3H, s), 5.40–5.60 (1H, brs), 6.50–7.90 (8H, m), 10.70 (1H, m).

EXAMPLE 24

2-(5-Carboxypentylcarbamoyl)-4-methyl-2H-1,4-benzothiazin-3(4H)one 1,1-dioxide was prepared substantially in the same manner as Example 5.

mp 132° to 134° C. (melt).

IR (Nujol): 3300, 3100, 1700, 1670 1650 cm$^{-1}$.

NMR (DMSO-d$_6$) ppm: 1.00–1.70 (6H, m), 1.90–2.40 (2H, m), 2.70–3.20 (2H, m), 3.43 (3H, s), 5.33 (1H, s), 7.20–7.90 (4H, m), 8.50 (1H, brs).

EXAMPLE 25

2-(2-Chlorophenylcarbamoyl)-4-methyl-2H-1,4-benzothiazin-3(4H)one 1,1-dioxide was prepared substantially in the same manner as Example 5.

mp 180° to 182° C. (melt).

IR (Nujol): 3350, 1670, 1660 cm$^{-1}$.

NMR (DMSO-d$_6$) ppm: 3.48 (3.48 (3H, s), 6.00 (1H, brs), 7.00–8.00 (8H, m), 10.22 (1H, s).

EXAMPLE 26

2-(3-Chlorophenylcarbamoyl)-4-methyl-2H-1,4-benzothiazin-3(4H)one 1,1-dioxide was prepared substantially in the same manner as Example 5.

mp 170° to 173° C. (melt).

IR (Nujol): 3350, 1690, 1600 cm$^{-1}$.

NMR (DMSO-d$_6$) ppm: 3.50 (3H, s), 5.55 (1H, s), 7.00–8.00 (7H, m), 8.31 (1H, s), 10.85 (1H, brs).

EXAMPLE 27

2-(4-Chlorophenylcarbamoyl)-4-propyl-2H-1,4-benzothiazin-3(4H)one 1,1-dioxide was prepared substantially in the same manner as Example 5.

mp 189° to 190° C. (melt).

IR (Nujol): 3350, 1700, 1680 cm$^{-1}$.

NMR (DMSO-d$_6$) ppm: 0.90 (3H, t, J=7 Hz), 1.30–1.90 (2H, m), 4.10 (2H, t, J=7 Hz), 5.50 (1H, s), 7.20–7.90 (8H, m), 10.95 (1H, brs).

EXAMPLE 28

2-(4-Carboxyhexahydrobenzyl)carbamoyl-4-methyl-2H-1,4-benzothiazin-3(4H)one 1,1-dioxide was prepared substantially in the same manner as Example 5.

mp 203° to 204° C. (melt).

IR (Nujol): 3380, 1690, 1670 cm$^{-1}$.

EXAMPLE 29

2-{3-(4-Chlorophenyl)carbazoyl}-3-methyl-2H-1,4-benzothiazin-3(4H)one 1,1-dioxide was prepared substantially in the same manner as Example 5.

mp 226° to 227° C. (melt).

IR (Nujol): 3310, 3280, 1698, 1640, 1630, 1595 cm$^{-1}$.

NMR (DMSO-d$_6$) ppm: 3.50 (3H, s), 5.47 (1H, s), 6.72 (2H, d, J=8 Hz), 7.20 (2H, d, J=8 Hz), 7.30–7.92 (4H, m), 8.26 (1H, brs), 10.42 (1H, s).

EXAMPLE 30

6-Chloro-2-(4-fluorophenylcarbamoyl)-4-methyl-2H-1,4-benzothiazin-3(4H)one 1,1-dioxide was prepared substantially in the same manner as Example 5.

mp 234° to 236° C. (melt).

IR (Nujol): 3300, 1700, 1660 cm$^{-1}$.

NMR (DMSO-d$_6$) ppm: 3.53 (3H, s), 5.63 (1H, s), 7.00–8.00 (7H, m), 10.56 (1H, s).

EXAMPLE 31

6-Chloro-4-methyl-2-(3-trifluoromethylphenylcarbamoyl)-2H-1,4-benzothiazin-3(4H)one 1,1-dioxide was prepared substantially in the same manner as Example 5.

mp 196° to 200° C. (melt).

IR (Nujol): 3320, 1695, 1670, 1610, cm$^{-1}$.

NMR (DMSO-d$_6$) ppm: 3.56 (3H, s), 5.68 (1H, s), 7.40–8.13 (7H, m), 11.30 (1H, s).

EXAMPLE 32

6-Chloro-2-(3-fluorophenylcarbamoyl)-4-methyl-2H-1,4-benzothiazin-3(4H)one 1,1-dioxide was prepared substantially in the same manner as Example 5.

mp 224° to 226° C. (melt).

IR (Nujol): 3300, 3100, 1680, 1660, 1620 cm$^{-1}$.

NMR (DMSO-d$_6$) ppm: 3.52 (3H, s), 5.63 (1H, s), 6.70–8.00 (7H, m), 11.02 (1H, s).

EXAMPLE 33

2-(3-Fluorophenylcarbamoyl)-4-methyl-2H-1,4-benzothiazin-3(4H)one 1,1-dioxide was prepared substantially in the same manner as Example 5.

mp 206° to 208° C. (melt).

IR (Nujol): 3400, 1705, 1690, 1610 cm$^{-1}$.

NMR (DMSO-d$_6$) ppm: 3.53 (3H, s), 5.60 (1H, s), 6.80–8.00 (8H, m), 11.00 (1H, s).

EXAMPLE 34

4-Methyl-2-(2-methylphenylcarbamoyl)-2H-1,4-benzothiazin-3(4H)one, 1,1-dioxide was prepared substantially in the same manner as Example 5.

mp 187° to 188.5° C. (melt).

IR (Nujol): 3300, 1670, 1650 cm$^{-1}$.

NMR (DMSO-d$_6$) ppm: 2.17 (3H, s), 3.48 (3H, s), 5.73 (1H, s), 6.96–8.0 (8H, m), 9.96 (1H, s).

EXAMPLE 35

4-Methyl-2-(4-methylphenylcarbamoyl)-2H-1,4-benzothiazin-3(4H)one 1,1-dioxide was prepared substantially in the same manner as Example 5.

mp 218° to 220° C. (melt).

IR (Nujol): 3300, 1675, 1650 cm$^{-1}$.

NMR (DMSO-d$_6$) ppm: 2.23 (3H, s), 3.50 (3H, s), 5.51 (1H, s), 7.0–8.0 (8H, m), 10.59 (1H, s).

EXAMPLE 36

4-Methyl-2-(2-pyridylcarbamoyl)-2H-1,4-benzothiazin-3(4H)one 1,1-dioxide was prepared substantially in the same manner as Example 5.

mp 216° to 217° C. (dec.).

IR (Nujol): 1640, 1580 cm$^{-1}$.

NMR (DMSO-d$_6$) ppm: 3.46 (3H, s), 5.81 (1H, s), 7.0–8.0 (7H, m), 8.18–8.43 (1H, m), 11.1 (1H, b.s).

EXAMPLE 37

A mixture of 2-ethoxycarbonyl-4-methyl-2H-1,4-benzothiazin-3(4H)one (6.22 g), 2-aminothiazole (7.43 g), and xylene (31 ml) was refluxed for 6 hours. After being cooled, the mixture was washed with 10% hydrochloric acid, water, dried over magnesium sulfate, and evaporated under reduced pressure. The residue was crystallized from diethyl ether and collected by filtration. The crude crystals were purified by recrystallization from acetonitrile to yield 1.17 g of 4-methyl-2-(2-thiazolylcarbamoyl)-2H-1,4-benzothiazin-3(4H)one.

mp 234° to 235° C. (melt).

IR (Nujol): 3300, 3200, 1685, 1660, 1580 cm$^{-1}$.

NMR (DMSO-d$_6$) ppm: 3.43 (3H, s), 4.63 (1H, s), 6.80–7.00 (6H, m), 12.50 (1H, brs).

EXAMPLE 38

A mixture of 2-ethoxycarbonyl-4-methyl-2H-1,4-benzothiazin-3(4H)one (2.4 g) and 4-fluoroaniline (1.59 g) was stirred for 5 hours at 180° to 185° C. After standing at room temperature, the reaction mixture was crystallized from diisopropyl ether and purified by recrystallization from diisopropyl ether to afford 0.94 g of 2-(4-fluorophenylcarbamoyl)-4-methyl-2H-1,4-benzothiazin-3(4H)one as a white crystal.

mp 158° to 160° C. (melt)
IR (Nujol): 3390, 1740, 1660 cm$^{-1}$.
NMR (DMSO-d$_6$) ppm: 3.43 (3H, s), 4.55 (1H, s), 7.00–7.80 (8H, m), 10.40 (1H, s).

EXAMPLE 39

To a solution of 1,1-carbonyldiimidazole (2.41 g) methyl-2H-1,4-benzothiazin-3(4H)one (3.01 g) in one portion below 10° C. The mixture was stirred for 30 minutes below 10° C. and for one hour at room temperature. To the clear solution was added 5-aminotetrazole (1.28 g). The resulting mixture was stirred for one hour at 80° to 90° C. and then allowed to cool to room temperature. The mixture was poured into 1% hydrochloric acid (200 ml) and extracted with ethyl acetate. The organic layers were extracted with aqueous sodium bicarbonate solution. The extracts were washed with ethyl acetate and adjusted to pH 2 with 10% hydrochloric acid. The separated solid was collected by filtration, washed with water, dried, and recrystallized from aqueous dimethylformamide (about 50%) to yield 1.50 g of 4-methyl-2-(5-tetrazolylcarbamoyl)-2H-1,4-benzothiazin-3(4H)one.

mp 247° to 248° C. (dec.).
IR (Nujol): 3250, 1695, 1660, 1610 cm$^{-1}$.
NMR (DMSO-d$_6$) ppm: 3.47 (3H, s), 4.67 (1H, s), 7.00–7.50 (4H, m), 12.40 (1H, brs).

EXAMPLE 40

6-Chloro-4-methyl-2-(2-phenetylcarbamoyl)-2H-1,4-benzothiazin-3(4H)one was prepared substantially in the same manner as Example 39.

mp 124° to 126° C. (melt).
IR (Nujol): 3270, 3100, 1670, 1640 cm$^{-1}$.
NMR (DMSO-d$_6$) ppm: 2.75 (2H, t, J=6 Hz), 3.16 (2H, q, J=6 Hz), 4.38 (1H, s), 7.00–7.50 (8H, m), 8.23 (1H, t, J=6 Hz).

EXAMPLE 41

4-Methyl-2-(3-trifluoromethylphenylcarbamoyl)-2H-1,4-benzothiazin-3(4H)one was prepared substantially in the same manner as Example 39.

mp 181° to 183° C. (melt).
IR (Nujol): 3300, 3150, 1680, 1640, 1610 cm$^{-1}$.
NMR (DMSO-d$_6$) ppm: 3.44 (3H, s), 4.63 (1H, s), 7.00–8.00 (8H, m), 10.68 (1H, s).

EXAMPLE 42

2-(4-Fluorophenylcarbamoyl)-2H-1,4-benzothiazin-3(4H)one was prepared substantially in the same manner as Example 39.

mp 210° to 212° C. (melt).
IR (Nujol): 3250, 3200, 3050, 1670, 1650 cm$^{-1}$.
NMR (DMSO-d$_6$) ppm: 4.22 (1H, s), 6.90–7.60 (8H, m), 10.31 (1H, s), 10.50 (1H, s).

EXAMPLE 43

2-(3,4-Dichlorophenylcarbamoyl)-4-methyl-2H-1,4-benzothiazin-3(4H)one was prepared substantially in the same manner as Example 39.

mp 191° to 193° C. (melt).
IR (Nujol): 3300, 3100, 1680, 1630 cm$^{-1}$.
NMR (DMSO-d$_6$) ppm: 3.47 (3H, s), 4.60 (1H, s), 7.00–8.00 (7H, m), 10.65 (1H, s).

EXAMPLE 44

4-Methyl-2-phenylcarbamoyl-2H-1,4-benzothiazin-3(4H)one was prepared substantially in the same manner as Example 39.

mp 124° to 126.5° C. (melt).
IR (Nujol): 3330, 1650, 1610 cm$^{-1}$.
NMR (DMSO-d$_6$) ppm: 3.42 (3H, s), 4.55 (1H, s), 7.00–7.70 (9H, m), 10.33 (1H, s).

EXAMPLE 45

4-Methyl-2-(2-phenetylcarbamoyl)-2H-1,4-benzothiazin-3(4H)one was prepared substantially in the same manner as Example 39.

mp 150° to 152° C. (melt).
IR (Nujol): 3300, 1665, 1645 cm$^{-1}$.
NMR (CDCl$_3$) ppm: 2.68 (2H, t, J=6 Hz), 3.48 (3H, s), 3.30–3.60 (2H, m), 4.20 (1H, s), 6.50–7.00 (1H, m), 7.00–7.60 (9H, m).

EXAMPLE 46

4-Methyl-2-(2-pyridylcarbamoyl)-2H-1,4-benzothiazin-3(4H)one was prepared substantially in the same manner as Example 39.

mp 141° to 143° C. (melt).
IR (Nujol): 3330, 1660, 1650 cm$^{-1}$.
NMR (DMSO-d$_6$) ppm: 3.42 (3H, s), 4.68 (1H, s), 7.00–7.60 (5H, m), 7.70–7.90 (2H, m), 8.30–8.50 (1H, m), 10.80 (1H, brs).

EXAMPLE 47

2-(5-Tetrazolylcarbamoyl)-2H-1,4-benzothiazin-3(4H)one was prepared substantially in the same manner as Example 39.

mp 244° to 246.5° C. (dec.)
IR (Nujol): 3550, 1680, 1655, 1640 cm$^{-1}$.
NMR (DMSO-d$_6$) ppm: 4.62 (1H, s), 6.89–7.42 (4H, m), 11.09 (1H, s), 12.52 (1H, brs).

EXAMPLE 48

2-(3,4-Dichlorophenylcarbamoyl)-4-methyl-2H-1,4-benzothiazin-3-(4H)one 1,1-dioxide (2.03 g) was prepared by the reaction of 2-(3,4-dichlorophenylcarbamoyl)-4-methyl-2H-1,4-benzothiazine-3(4H)one (3.67 g) in a mixture of acetic acid (20 ml) and chloroform (20 ml) with potassium permanganate (2.05 g), and by treating the reaction mixture substantially in the same manner as Example 5. The object compound was identified with an authentic sample of Example 21.

We claim:
1. A compound of the formula or its pharmaceutically acceptable salt:

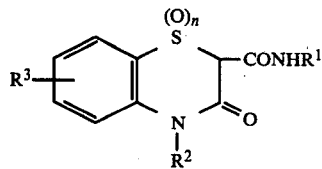

wherein
- $R^1$ is lower alkyl which may have one or more substituents selected from carboxy, phenyl and carboxy(lower)cycloalkyl;
  phenyl which may have one or more substituents selected from halogen, lower alkyl, halo(lower)alkyl and lower alkoxy;
  halophenylamino; or
  5- or 6-membered heterocyclic group containing at least one hetero atom selected from oxygen, nitrogen and sulfur;
- $R^2$ is hydrogen, lower alkyl, lower alkylamino(lower)alkyl, phenyl or phenyl(lower)alkyl;
- $R^3$ is hydrogen, halogen, lower alkyl or lower alkoxy; and
- n is an integer 0 to 2.

2. A compound according to claim 1, wherein
- $R^1$ is lower alkyl which may have one or more substituents selected from carboxy, phenyl and carboxy(lower)cycloalkyl; phenyl which may have one or more substituents selected from halogen, lower alkyl, halo(lower)alkyl and lower alkoxy; halophenylamino; or 5 or 6 membered heterocyclic group containing at least one hetero atom selected from oxygen, nitrogen and sulfur
- $R^2$ is hydrogen, lower alkyl or lower alkylamino(lower)alkyl;
- $R^3$ is hydrogen, halogen or lower alkoxy; and
- n is an integer 0 or 2.

3. A compound according to claim 2, wherein $R^1$ is mono- or di- halophenyl, $R^2$ is lower alkyl, $R^3$ is hydrogen and n is an integer of 2.

4. A compound according to claim 3, wherein
- $R^1$ is mono or di-halophenyl, and
- $R^2$, $R^3$ and n are each as defined in claim 3.

5. A compound according to claim 4, wherein $R^1$ is 3,4-dichlorophenyl, $R^2$ is methyl, $R^3$ is hydrogen and n is an integer of 2.

6. A pharmaceutical composition for inhibition of contact hypersensitivity comprising as an active ingredient an effective amount of a compound of claim 1 or its pharmaceutically acceptable salt in admixture with a pharmaceutically acceptable carrier.

* * * * *